(12) United States Patent
Carey et al.

(10) Patent No.: US 10,599,865 B2
(45) Date of Patent: Mar. 24, 2020

(54) SYSTEMS AND METHODS FOR PROTECTING PERSONAL INFORMATION

(71) Applicant: Intertrust Technologies Corporation, Sunnyvale, CA (US)

(72) Inventors: W. Knox Carey, Mountain View, CA (US); Jarl A. Nilsson, Mountain View, CA (US); Bart Grantham, Mountain View, CA (US)

(73) Assignee: Intertrust Technologies Corporation, Sunnyvale, CA (US)

( * ) Notice: Subject to any disclaimer, the term of this patent is extended or adjusted under 35 U.S.C. 154(b) by 771 days.

(21) Appl. No.: 15/209,448

(22) Filed: Jul. 13, 2016

(65) Prior Publication Data

US 2017/0017805 A1 Jan. 19, 2017

Related U.S. Application Data

(60) Provisional application No. 62/192,022, filed on Jul. 13, 2015.

(51) Int. Cl.
| | |
|---|---|
| *G06F 7/00* | (2006.01) |
| *G06F 17/30* | (2006.01) |
| *G06F 21/62* | (2013.01) |
| *G16B 20/00* | (2019.01) |
| *G16B 50/00* | (2019.01) |

(52) U.S. Cl.
CPC ......... *G06F 21/6245* (2013.01); *G16B 20/00* (2019.02); *G16B 50/00* (2019.02)

(58) Field of Classification Search
CPC .............................. G06F 21/6245; G06F 19/18
USPC ....................................................... 707/784
See application file for complete search history.

(56) References Cited

U.S. PATENT DOCUMENTS

| | | | |
|---|---|---|---|
| 5,892,900 A | 4/1999 | Ginter et al. | |
| 7,430,585 B2 | 9/2008 | Sibert | |
| 2003/0043905 A1* | 3/2003 | Nakayama | H04N 1/411 375/240.04 |
| 2004/0014109 A1* | 1/2004 | Pericak-Vance | C12Q 1/6883 435/6.16 |
| 2004/0050929 A1* | 3/2004 | Fayfield | G06F 21/33 235/380 |

(Continued)

FOREIGN PATENT DOCUMENTS

WO  WO 2005/124624 A1  12/2005

OTHER PUBLICATIONS

International Preliminary Report on Patentability dated Jan. 25, 2018, in related PCT Application No. PCT/US2016/042136 (7 pages).

(Continued)

*Primary Examiner* — Binh V Ho
(74) *Attorney, Agent, or Firm* — Finnegan Henderson Farabow Garrett & Dunner LLP

(57) ABSTRACT

The present disclosure relates to systems and methods for facilitating trusted handling of genomic bioinformatics, and/or other sensitive information. Certain embodiments may facilitate policy-based governance of access to and/or use of information through enforced disclosure accounting processes. Among other things, embodiments of the disclosed systems and methods may mitigate the potential for various attacks, including reidentification attacks targeting particular individuals associated with information included in a genomic data set.

7 Claims, 4 Drawing Sheets

(56) References Cited

U.S. PATENT DOCUMENTS

| | | | |
|---|---|---|---|
| 2004/0117264 A1* | 6/2004 | Chess | G06F 21/6245 705/304 |
| 2008/0213551 A1* | 9/2008 | Funicelli | B44C 1/1737 428/209 |
| 2009/0164649 A1* | 6/2009 | Kawato | G06F 21/6218 709/229 |
| 2010/0122314 A1* | 5/2010 | Zhang | G06F 21/554 726/1 |
| 2010/0161607 A1* | 6/2010 | Singh | G16B 50/00 707/737 |
| 2010/0161664 A1* | 6/2010 | Puhl | H04L 9/3231 707/781 |
| 2012/0157324 A1* | 6/2012 | Lizardi | C12Q 1/6886 506/2 |
| 2013/0191493 A1 | 7/2013 | Le et al. | |
| 2013/0231960 A1 | 9/2013 | Lorsch | |
| 2013/0307670 A1 | 11/2013 | Ramaci | |
| 2014/0013442 A1 | 1/2014 | Ito | |
| 2014/0289536 A1 | 9/2014 | MacCarthy et al. | |
| 2018/0046753 A1* | 2/2018 | Shelton | G16H 80/00 |

OTHER PUBLICATIONS

International Search Report and Written Opinion dated Oct. 12, 2016; PCT Application No. PCT/US2016/042136; 8 pages.
Extended European Search Report dated Apr. 26, 2018, for related European Patent Application No. 16825127.0; (7 pages).

* cited by examiner

SYSTEMS AND METHODS FOR PROTECTING PERSONAL INFORMATION

RELATED APPLICATIONS

This application claims the benefit of priority under 35 U.S.C. § 119(e) to U.S. Provisional Patent Application No. 62/192,022, filed Jul. 13, 2015, and entitled "SYSTEMS AND METHODS FOR PROTECTING AGAINST RE-IDENTIFICATION", which is hereby incorporated by reference in its entirety.

COPYRIGHT AUTHORIZATION

Portions of the disclosure of this patent document may contain material which is subject to copyright protection. The copyright owner has no objection to the facsimile reproduction by anyone of the patent document or the patent disclosure, as it appears in the U.S. Patent and Trademark Office patent file or records, but otherwise reserves all copyright rights whatsoever.

SUMMARY

The present disclosure relates generally to systems and methods for facilitating trusted handling of personal information. More specifically, but not exclusively, the present disclosure relates to systems and methods for enabling secure, governed, and/or audited use of personal information that may include genomic and/or bioinformatic information.

Genetic testing is moving from detection of Single Nucleotide Polymorphisms ("SNPs")—isolated individual chemical differences in genetic code—to Whole Genomic Sequencing ("WGS"), which records every base pair in a genetic sequence. Genomic sequencing information may be used in connection with a variety of applications including, for example, molecular and evolutionary biology studies. For example, in molecular biology studies, genomic information may be used in connection with identifying new genes, identifying potential drug targets, identifying genetic associations with certain diseases and/or conditions, and/or the like. In many circumstances, genomic information and/or bioinformatic information may comprise personal information relating to one or more associated individuals.

Genomic and/or bioinformatic information may be included in an electronic resource. The electronic resource may be directly and/or indirectly accessible by one or more users and may comprise personal information relating to one or more individuals. In certain embodiments, to improve individual privacy and security of personal information, derived resources may be generated based on the available electronic resource and presented to requesting users. In certain embodiments, the derived resource may comprise a resource that is computed from an original and/or otherwise static resource by a computation before presentation to a user in a manner designed to preserve the privacy of associated personal information.

Computations that produce derived resources may be expressed as computer-readable instructions for operating on an original resource to produce a particular view of the original resource and/or a result based on the original resource. Although, in some embodiments, computations may involve the use of mathematical calculations, the term "computation," as used herein, is not so limited, and may encompass any set of instructions, procedures, methods, or other mechanisms for producing a particular presentation of the original resource (e.g., one that does not disclose all of the information in the original resource.). For example, if the original resource were a list of "name-birthdate-height" triplets, an example of a computation would be any suitable way of instructing a rendering application to display only a list of "birthdate-height" pairs (i.e., to omit the "name" data from the display). Another example of a computation would be a set of instructions that would operate on the original dataset to generate the median height and the average height for display to a requesting user.

In some embodiments, computations may be securely associated with a resource, which may be distributed to a user and/or securely accessed by a requesting user. In at least one example, a human genome sequence may be encrypted and sent to a researcher who wishes to incorporate information about the sequence into a study. As part of the original package, the researcher may receive a set of computations that provide various allowed views of the data. The researcher, however, may wish to execute a newly-created computation that, when run against the sequence, will provide an estimated risk of a particular disease based on information obtained from several genes. The researcher's computation may be sent to the owner of the genome sequence and, assuming the owner agrees, may be securely associated with the sequence and sent back to the researcher in a form that allows the researcher to run the computation against the sequence in accordance with associated rules.

Access to information included in a resource may be managed according to one or more articulated policies and/or rules associated with the resource. In certain embodiments, articulated policies and/or rules may be enforced in connection with generating derived resources based on a resource using an associated computation. Consistent with embodiments disclosed herein, policies and/or rules associated with a resource may be further used in connection with managing privacy of individuals associated with a resource (e.g., individuals associated with a genomic data resource) and/or the security of associated personal information.

Derived resources generated using policy-enforced processes may help preserve the privacy of an original resource and/or associated personal information included therein. Consistent with embodiments disclosed herein, the known history of computations that have been bound to a resource may be analyzed to ensure that only a desired and/or threshold amount of disclosure occurs. In some situations, one or more computations may be individually innocuous, but may reveal more personal information relating to one or more individuals than desired when used together. Accordingly, in one example, an enforced privacy-preserving policy associated with a resource may decrease the resolution of, or otherwise reduce the information content of, the data revealed by successive computations.

Consistent with embodiments of the disclosed systems and methods, disclosure accounting may be used to ensure that a desired and/or threshold amount of disclosure occurs relating to a resource in accordance with an associated enforced policy. In certain embodiments, privacy accounting systems and methods may maintain records about access to a resource over time that may serve as a basis for making policy enforcement decisions about future access to the resource. For example, in some embodiments, a disclosure budget may be established that may be exhausted as more and more information relating to a resource is revealed, disabling and/or otherwise limiting access when the disclosure budget is exhausted.

BRIEF DESCRIPTION OF THE DRAWINGS

The inventive body of work will be readily understood by referring to the following detailed description in conjunction with the accompanying drawings, in which.

DETAILED DESCRIPTION

Figure 1:
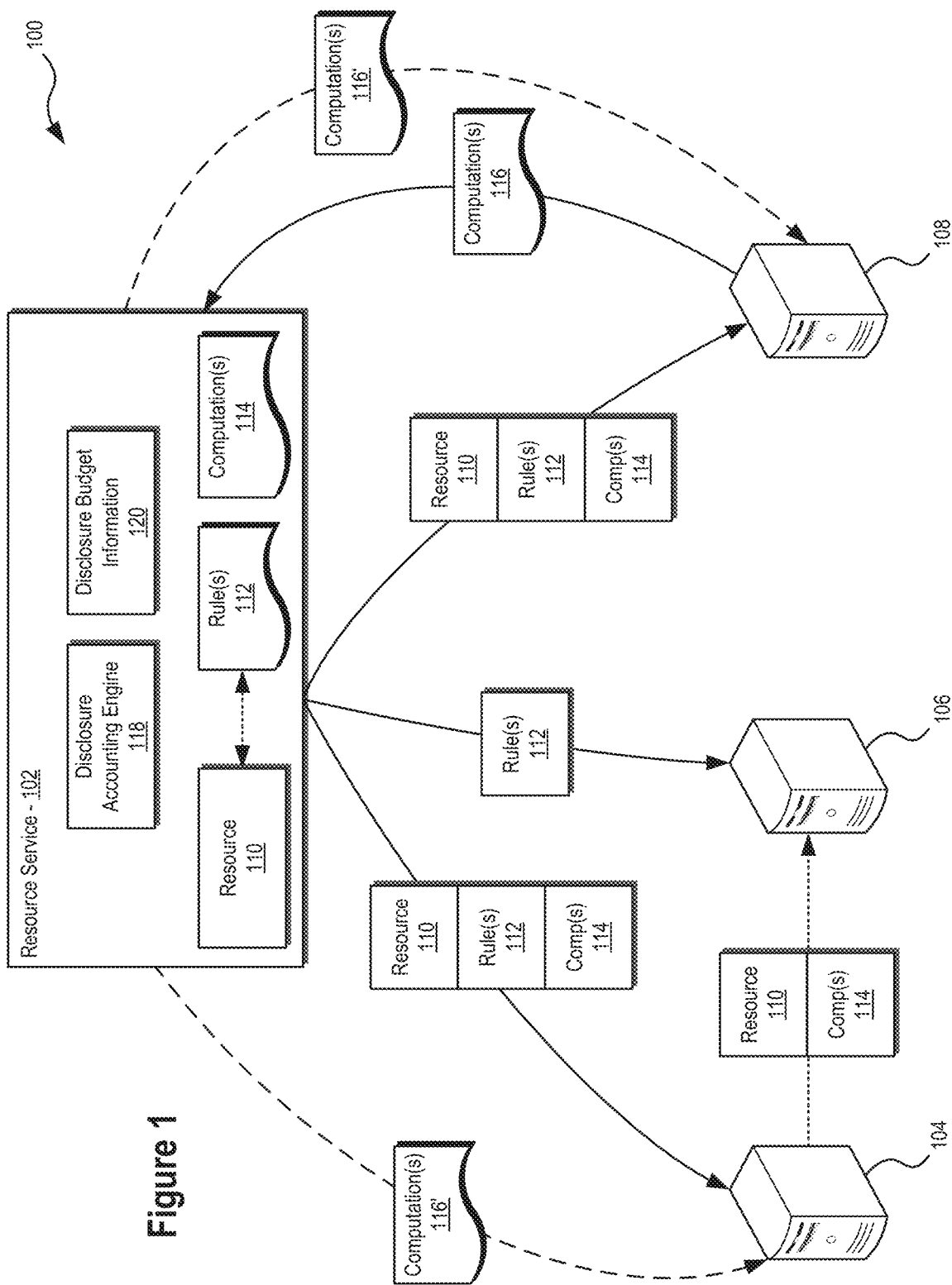
FIG. 1 illustrates an exemplary architecture for interacting with a resource consistent with embodiments disclosed herein.

A detailed description of systems and methods consistent with embodiments of the present disclosure is provided below. While several embodiments are described, it should be understood that the disclosure is not limited to any one embodiment, but instead encompasses numerous alternatives, modifications, and equivalents. In addition, while numerous specific details are set forth in the following description in order to provide a thorough understanding of the embodiments disclosed herein, some embodiments can be practiced without some or all of these details. Moreover, for the purpose of clarity, certain technical material that is known in the related art has not been described in detail in order to avoid unnecessarily obscuring the disclosure.

The embodiments of the disclosure may be understood by reference to the drawings, wherein like parts may be designated by like numerals. The components of the disclosed embodiments, as generally described and illustrated in the figures herein, could be arranged and designed in a wide variety of different configurations. Thus, the following detailed description of the embodiments of the systems and methods of the disclosure is not intended to limit the scope of the disclosure, as claimed, but is merely representative of possible embodiments of the disclosure. In addition, the steps of any method disclosed herein do not necessarily need to be executed in any specific order, or even sequentially, nor need the steps be executed only once, unless otherwise specified.

Systems and methods are presented that facilitate secure, governed, and/or audited use of an electronic resource that may include genomic, bioinformatics, and/or other information. In certain embodiments, the disclosed systems and methods can be used to enable policy-based governance of access to and/or use of genomic or other sensitive data and/or protect privacy of personal information associated with such data. In some embodiments, the disclosed systems and methods may use disclosure accounting processes to manage an amount of personal data revealed to one or more requesting users. For example, in certain embodiments, a disclosure budget may be established that may be exhausted as personal information associated with a genomic data resource is revealed to one or more requesting users. When the disclosure budget is exhausted, access to the resource may be disabled, managed, and/or otherwise restricted. In some embodiments, managed access to a genomic data resource using disclosure accounting processes may be implemented using one or more policies associated with the resource. It will be appreciated that these systems and methods are novel, as are many of the components, systems, and methods employed therein.

As used herein, the terms "genomic data," "genomic resource," "genomic information," "genome," and/or the like may generally refer to data expressing, representing, and/or derived from the entirety or a portion of a genome or genome sequence. This data may include, without limitation, information encoded in chemical structures such as DNA, mRNA, and proteins, as well as related regulatory information such as methylation status. As used herein, the term "genome" may refer to an organism's hereditary information. A genome may be encoded in DNA or RNA, and may be represented as mRNA or as protein sequences derived from these nucleic acid sequences. The term "genome" may include both genes and non-coding sequences. When applied to a specific organism, the term "genome" can refer to genomic data from normal cells— including mitochondrial DNA—and also genomic data from related cells such as tumors and other organisms of the microbiome. Although embodiments of the disclosed systems and methods are discussed herein in connection with genomic data, it will be appreciated that the disclosed systems and methods may also be used in connection with any other suitable information, including any other type of bioinformatic information or personal or sensitive information.

In certain embodiments, the systems and methods described herein can, for example, be used in connection with digital rights management ("DRM") technologies such as those described in commonly assigned U.S. Pat. No. 8,776,216, entitled "Digital Rights Management Engine Systems and Methods," and filed Oct. 18, 2006 ("the '216 patent"), service orchestration and DRM technologies such as those described in commonly assigned U.S. Pat. No. 8,234,387, entitled "Interoperable Systems and Methods for Peer-to-Peer Service Orchestration," and filed Jun. 7, 2004 ("the '387 patent"), information governance technologies such as those described in commonly assigned U.S. patent application Ser. No. 13/444,624, entitled "Information Security Systems and Methods," and filed Apr. 11, 2012 ("the '624 application"), and/or information processing technologies such as those described in commonly assigned U.S. patent application Ser. No. 13/654,349, entitled "Systems and Methods for Protecting and Governing Genomic and Other Information," and filed Oct. 17, 2012 ("the '349 application") (the contents of the '216 patent, the '387 patent, the '624 application, and the '349 application hereby being incorporated by reference in their entireties), as well as in other contexts.

Reidentification Overview

To improve the value of genomic data in connection with genomic studies, disparate datasets may be federated to provide sufficient statistical power for scientific analysis. For example, certain interesting and/or deleterious genetic variants may be relatively rare, and it may be statistically unlikely that a single genomic dataset contains enough samples to draw meaningful conclusions. Accordingly, use of multiple federated genomic datasets may increase the statistical likelihood of drawing meaningful conclusions from the datasets in connection with an associated genomic study.

Federating genomic datasets and sharing genomic data amongst multiple institutions may introduce certain privacy considerations relating to the disclosure of personal information associated with and/or otherwise included in the data. For example, in some circumstances, a reidentification attack may be initiated by a malicious attacker using a query mechanism designed to extract sufficient information to determine whether a particular individual's information is included in a given dataset. Disclosure of such information may be harmful to the individual. For example, determining that an individual's information is in a database of HIV/

AIDS patients could undesirably reveal health status information and/or violate privacy laws or institutional policies.

Genomic Resource APIs and Reidentification

Reidentification attacks may be mounted using seemingly innocuous means and/or via seemingly innocent queries. User access to a genomic resource may be facilitated by a suitable application program interface ("API"). For example, the "Beacon API," developed by the Data Working Group of the Global Alliance for Genomics and Health ("GA4GH") may be used to interact with federated genomic data associated with multiple institutions. The Beacon API service is designed to accept a query of the form "Do you have any genomes with an allele G in position 12,345,678 on chromosome 9?" or the like and respond with one of "Yes" or "No." The query may be intended to apply to all genomes in a given dataset. Therefore, a significantly large dataset may contribute to obscuring individual contributions. A site implementing such a service may be referred to as a "beacon" or a beacon service.

As noted above, variants of interest are often relatively rare, and an individual may have unique variants that may act as a sort of genetic fingerprint for identification of the individual and/or their close relatives. Queries of the form used by a beacon service may be individually innocuous, but may nevertheless reveal more personal information relating to a particular individual than desired when targeted and used repeatedly. For example, individuals contributing as little as 0.1% of the data in a dataset may be resolved through multiple targeted queries, even when their data is mixed with that of thousands of other individuals. The potential for such undesirable disclosure may reduce the availability of valuable federated datasets, as organizations may choose to manage their data in strictly siloed access-controlled environments.

Policy-Managed Methods for Mitigating Reidentification

Systems and methods disclosed herein provide for policy-based governance of access to and/or use of data resources that may mitigate the potential for successful reidentification attacks targeted at such data. FIG. 1 illustrates an exemplary architecture 100 for interacting with a resource consistent with embodiments disclosed herein. As illustrated, the architecture 100 may include a resource service 102 and/or one or more remote systems 104-108. The resource service 102 may provide a variety of functions allowing users of the remote systems 104-108 to process, analyze, and/or otherwise interact with a managed resource 110, which may comprise genomic data.

In certain embodiments, the remote systems 104-108 may be communicatively coupled with the resource service 102 via a network. The network may comprise a variety of network communication devices and/or channels and may use any suitable communication protocols and/or standards facilitating communication between the remote systems 104-108, the resource service 102, and/or one or more other systems. For example, the network may comprise the Internet, a local area network, a virtual private network, and/or any other communication network utilizing one or more electronic communication technologies and/or standards (e.g., Ethernet or the like). In some embodiments, the network may comprise a wireless carrier system, such as a personal communications system ("PCS"), and/or any other suitable communication system incorporating any suitable communication standards and/or protocols. In further embodiments, the network may comprise an analog mobile communications network and/or a digital mobile communications network utilizing, for example, code division multiple access ("CDMA"), Global System for Mobile Communications or Groupe Speciale Mobile ("GSM"), frequency division multiple access ("FDMA"), and/or time divisional multiple access ("TDMA") standards. In certain embodiments, the network 102 may incorporate one or more satellite communication links. In yet further embodiments, the network may use IEEE's 802.11 standards, Bluetooth®, ultra-wide band ("UWB"), Zigbee®, and/or any other suitable standard or standards.

The remote systems 104-108 and/or the resource service 102 may comprise a variety of computing devices and/or systems, including any computing system or systems suitable to implement the systems and methods disclosed herein. The connected systems 102-108 may comprise a variety of computing devices and systems, including laptop computer systems, desktop computer systems, server computer systems, distributed computer systems, smartphones, tablets, and/or the like. It will be appreciated that any suitable configuration of computing systems and storage media could be used in connection with the connected systems 102-108, including without limitation, a single server or cluster of servers, and/or a distributed collection of heterogeneous computer systems connected by a variety of networks (e.g., such as the Internet, public and/or private networks, and/or the like).

In certain embodiments, the remote systems 104-108 and/or the resource service 102 may comprise at least one processor system configured to execute instructions stored on an associated non-transitory computer-readable storage medium. As discussed in more detail below, the remote systems 104-108 and/or the resource service 102 may further comprise a secure processing unit ("SPU") configured to perform sensitive operations such as trusted credential and/or key management, secure policy management, and/or other aspects of the systems and methods disclosed herein. The remote systems 104-108 and/or the resource service 102 may further comprise software and/or hardware configured to enable electronic communication of information between the devices and/or systems 102-108 via the network using any suitable communication technology and/or standard.

The resource service 102 may be configured to store, manage, process, distribute, and/or update resources 110 stored thereon. In certain embodiments, the resource service 102 may be associated with one or more cloud-based systems for the trusted storage and analysis of genetic and/or other information, and may incorporate embodiments of the systems and methods disclosed in connection with the '349 application.

An application executing on the remote systems 104-108 may enable a user of the systems to interact with the resource service 102 in connection with performing various workflow processes and/or analyses using the resource 110. For example, in certain embodiments, the remote systems 104-108 may be configured to issue certain requests/queries to the resource service 102 directing the resource service 102 to perform certain processes and/or operations using the resource 110 stored thereon. Results of the processes and/or operations may be generated in accordance with applicable rules and/or policies 112 and returned to the remote systems 104-108 from the resource service 102. In certain embodiments, such results may obfuscate, anonymize, and/or otherwise filter personal information and/or other phonotypical data associated with the resource 110, such that users of the remote systems 104-108 may not ascertain and/or readily ascertain personal information from results derived from the resource 110.

In at least one example, the resource 110, which may comprise scientific research data, healthcare records, genomic information media content, and/or the like, may be packaged together with a set of computation(s) 114 and rule(s) 112 by the resource service 102 (e.g., as an owner or distributor of the resource 110 and/or an entity acting on behalf thereof). For example, the resource 110 may be encrypted, digitally signed, and/or otherwise protected, and securely associated with the computation(s) 114 and rule(s) 112. The resource 110 may be distributed together with the computation(s) 114 and rule(s) 112 to a remote system 104. Alternatively, or in addition, the resource 110 may be distributed to a remote system 106 independently of computation(s) 114 and/or rule(s) 112. Another remote system 108 may propose additional computations 116 pertaining to the resource 110 to the resource service 102. The resource service 102 may securely associate the computation 116 with the resource 110 (e.g., in the form proposed by the remote system 108, in a modified form, with additional pre or post computations required to be performed, and/or the like), and distribute or make available for distribution such computations 116' for use in connection with the resource 110.

In certain embodiments, the resource service 102 and/or the remote systems 104-108 may enforce one or more policies and/or rules 112 in connection with performing computation(s) 114, 116, and/or 116' associated with a resource 110. Consistent with embodiments disclosed herein, a disclosure accounting engine 118 executing on the resource service 102 and/or the remote systems 104-108 may be configured to manage the disclosure of information from the resource 110 to requesting users. The disclosure accounting engine 118 may analyze a query and/or an associated computational result, determine an amount of disclosure associated with the result (e.g., an informational value of the result), analyze and/or otherwise update disclosure budget information 120 in relation to the determined amount of disclosure, and/or allow, disallow, and/or otherwise restrict and/or limit access to the result based on the same. For example, in certain embodiments, a disclosure budget may be established and reflected in the disclosure budget information 120 that may be exhausted as personal information associated with a genomic data resource is revealed to one or more requesting users. When the disclosure budget is exhausted, access to the resource may be disabled, managed, and/or otherwise restricted.

Computations associated with a governed resource may be performed in a protected processing environment. In some embodiments, the owner/packager of a resource may distribute a virtual secure package for various consuming users to process. Associated computations and/or rule/policy evaluation may occur within a protected processing environment at the consuming users' systems. In further embodiments, an owner/packager of a resource may perform some or all of the computations in its own protected processing environment and return associated results to a requester (e.g., based on attributes of the requester such as an authenticated identity and/or the like). Alternatively, or in addition, the computations on a resource may be performed by a delegated entity to whom the resource originator has delegated authority to manage and/or otherwise perform the computations.

Figure 2:
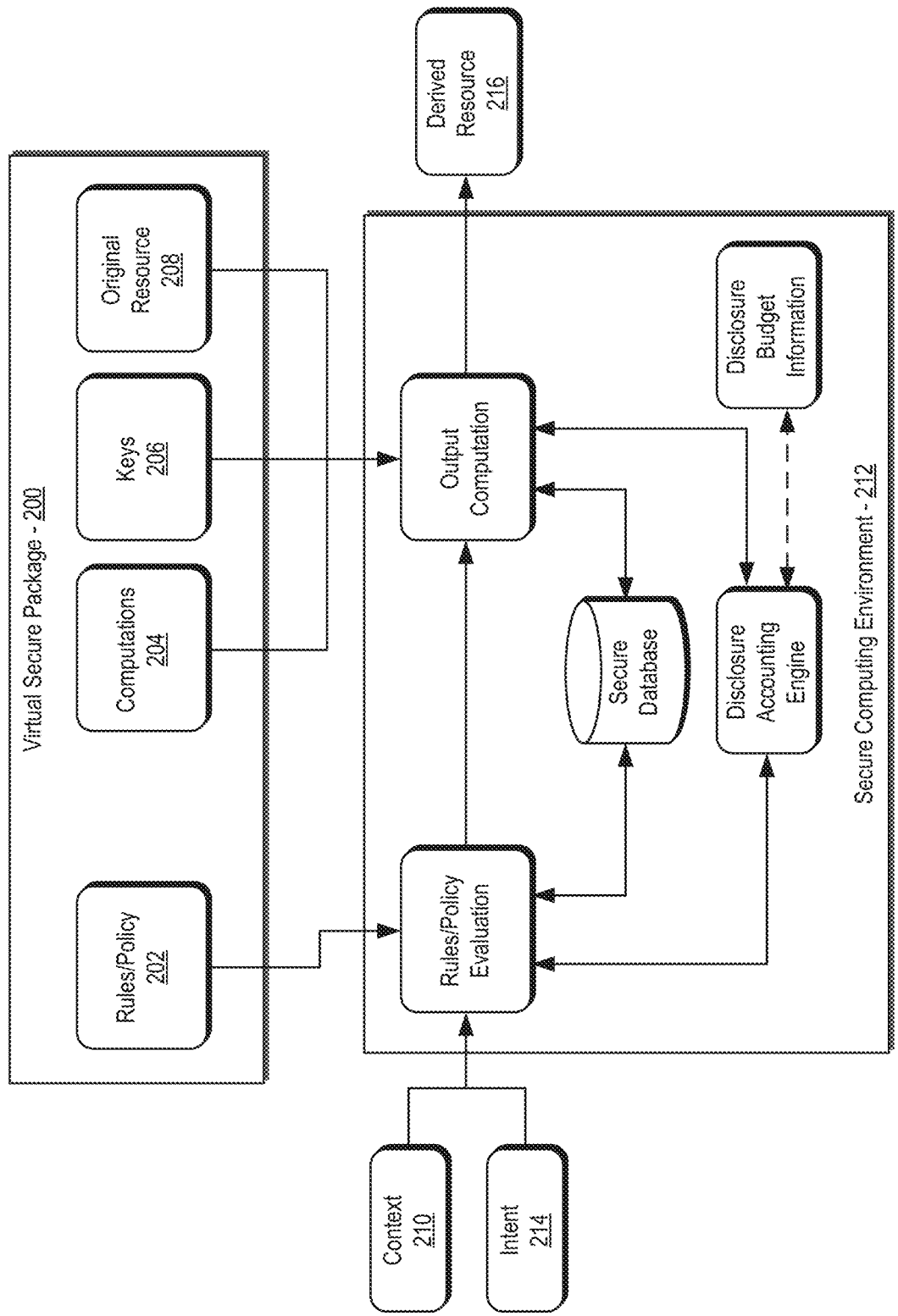
FIG. 2 illustrates an illustrative system for providing access to derived resources consistent with embodiments disclosed herein.

FIG. 2 shows an illustrative system for providing access to derived resources consistent with embodiments disclosed herein. As illustrated, a virtual secure package 200 may comprise rules and/or policy information 202, computations 204, keys 206 and/or an original resource 208. In certain embodiments, the various components 202-208 may be distributed either together and/or separately, and may be persistently associated with one another using any suitable cryptographic technique.

A request to perform a computation and generate a derived resource 216 may be received by a secure computing environment 212. The request may include context information 210 that may include, for example, information regarding an environment in which the resource derivation is being performed (e.g., information gathered from a user of the system and/or the like). The request may further include intent information 214 that may include, for example, a specified use that a requesting user wishes to make of the data. In some embodiments, the request may further comprise information that may be used to determine, at least in part, which policies and/or rules 202 and/or computations 204 should be evaluated in connection with performing the computation.

Upon receipt of the request, the secure computing environment 212 may process the virtual secure package 200 in accordance with its associated rules and/or policies 202 to yield the derived resource 216. In certain embodiments, associated rules and/or policies 202 may be evaluated to determine whether the request is permitted. In some embodiments, this evaluation may use information maintained in a secure database associated with the secure computing environment 212. For example, based on associated rules and/or policies 202, authentication information included in the secure database may be accessed to authenticate a received request and/or a requesting user.

In further embodiments, the rules and/or policies 202 may articulate a requirement that a request be approved by a disclosure accounting engine prior to generating and/or transmitting a derived resource 216 to a requesting user. In certain embodiments, the disclosure accounting engine may analyze a request and/or a resulting derived resource 216 to determine an associated amount of disclosure and/or an information value of the disclosure. In connection with determining whether to approve the request, the disclosure accounting engine may access associated disclosure budget information. Based on the accessed disclosure budget information, the disclosure accounting engine may allow, disallow, restrict, and/or otherwise manage access to the resource 208 and/or the derived resource 216.

Authentication and Auditing

In some embodiments, reidentification attacks may be mitigated by ensuring that identities of individuals querying a dataset are known and/or otherwise authenticated prior to allowing access to a dataset. Similarly, access to a dataset may be recorded and/or otherwise audited to better facilitate forensic investigation of breaches. In certain embodiments, authentication and/or auditing may be used in connection with disclosure accounting methods to reduce the likelihood of malicious attacks including, without limitation, reidentification attacks.

Disclosure Accounting and Disclosure Budgets

Consistent with embodiments disclosed herein, disclosure accounting may be used in connection with managing an amount of personal information revealed to one or more requesting users in connection with requests for computations on derived resources. In some embodiments, disclosure accounting may, among other things, record information relating to access to a resource over time that may serve as a basis for making policy determinations about future access to the resource. In certain embodiments, a disclosure budget may be established that may be exhausted as personal information associated with a resource is revealed to one or more requesting users. In some embodiments, disclosure accounting may allow for management of the disclosure of personal information even in circumstances when queries relating to a resource are made anonymously.

Disclosure Accounting Based on Access Requests

Reidentification of a given individual using queries to a dataset may not be possible if information relating to the individual (or a closely-related individual) is not in the dataset. Moreover, if a query against a dataset does involve a particular individual's data, a response to the query may not necessarily reveal information regarding the individual.

In certain embodiments, these characteristics of reidentification may facilitate disclosure accounting based on a number of access requests that involve a particular individual. For example, a counter associated with a given individual may be incremented each time a response to a query (e.g., a beacon query) involves the individual in some way. Certain queries, such as queries using a Beacon API, may involve an entire available dataset. Accordingly, in some embodiments, the counter may be incremented for a particular individual when a Beacon API query returns a "yes"—that is, when the individual has a particular allele being queried. Counter values may be compared with certain disclosure budgets associated with various individuals, and responses may be provided based on whether the disclosure budgets are exceeded or not exceeded according to enforced policy.

In some circumstances, a Beacon API query returning a "no" may still be informative to a certain degree in connection with a reidentification attack. For example, if an attacker is interested in determining the presence in a dataset of a person with allele G in position 12,345,678 on chromosome 9, the attacker could directly inquire about this allele, seeking the answer "Yes". Alternatively, the attacker could ask about alleles A, C, and T, looking for "No" answers. Each "No" return may increase the attacker's knowledge about the presence of the desired allele, albeit imperfectly.

The biological phenomenon of evolutionary conservation may be incorporated into embodiments of the disclosure accounting processes described herein to account for certain queries that may not return results useful in reidentification. Many alleles in the human genome are "highly conserved," meaning that they almost never change because of their importance to basic life functions. For example, a variant in a gene that codes for a protein integral to adenosine triphosphate ("ATP") synthesis might render an organism's cells incapable of storing energy, thus making basic metabolism impossible. Such a mutation could not appear in a living organism, because no embryo with this mutation could survive. There are other, less deleterious mutations that may survive, although with a very low frequency of occurrence. A Beacon API query for a highly conserved allele, may not be particularly informative about a given individual, and thus may be weighted less significantly in connection with identifying reidentification attacks.

Disclosure Accounting and Information Metrics

Consistent with embodiments disclosed herein, disclosure accounting may be based on information included in results generated in response to a query. For example, a query and/or an associated computational result may be analyzed to determine an amount of disclosure and/or an informational value associated with the result. Based on the determined amount of information, disclosure budget information may be analyzed and/or otherwise updated in relation to the determined amount of disclosure, and access to the result may be allowed, disallowed, and/or otherwise restricted based on the same. For example, in certain embodiments, a disclosure budget may be established that may be exhausted as personal information associated with a genomic data resource is revealed to one or more requesting users. When the disclosure budget is exhausted, access to the resource may be disabled, managed, delayed, and/or otherwise restricted.

In certain embodiments, an information metric may be used to reflect an amount of disclosure associated with a particular result. Some embodiments of the disclosed systems and methods may use a Shannon metric as an information metric. See C. Shannon and W. Weaver, *The Mathematical Theory of Communication*, Univ. of Illinois Press, Chicago, 1949.

In an informal sense, information conveyed by an event measures how "surprising" the event is. For example, a coin flip may be associated with a probability p of landing on heads. The cases p=0 or p=1 may correspond to tails and heads, respectively, so coin flips with these probabilities are deterministic. For a coin with a probability p=0.95 of heads, it is not surprising that a flip will result in heads most of the time. For a fair coin with p=0.5, the maximum "surprise" is achieved because it is equally likely that the coin falls on heads or tails. A formal definition of an information metric consistent with the disclosed embodiments may be used to reflect these intuitive properties.

In one example relating to genomic data queries, an exemplary allele must be A for an organism to be viable. In such cases, there may be little to no randomness in this allele—it may be deterministic in the same way that a coin with p=1 is deterministic. Accordingly, learning that an individual organism has the A allele provides no information beyond what we could have inferred from the fact that the organism is (or was) alive. This limits its utility in connection with a reidentification attack.

On the other hand, if an allele is rare (or extremely rare), an individual with this variant may stand out relatively clearly in the dataset, in a similar manner to which a single "tails" in a list of 1000 coin flips would stand out. A query involving this particular variant that involves a given individual therefore is highly informative about the individual's data being present in the dataset. An allele that is equally likely to be C or T in a given population is not particularly informative about the individual holding the C or T.

Based on the above, an information metric for use in connection with disclosure accounting and/or reidentification mitigation may increase as a queried allele's frequency decreases in a dataset and vice-versa. The lower the frequency of a given allele, the less the likelihood (i.e., the more surprising) that an individual has that allele, and thus the more significant the presence of that allele is in detecting the presence of that individual.

Additive Information Metrics

As discussed above, the Shannon information metric may be used in connection with the disclosed embodiments as a formulation for capturing the information content of an event based on its likelihood. In certain embodiments, the metric may be expressed according to:

$$I(x) = -\log p(x)$$

where x represents an event (e.g. the given individual has allele A in position 12,345,678 on chromosome 9), p(x) is the probability of the event x, and the base of the logarithm is chosen to give the desired units for the information metric. In some embodiments, base-2 logarithms may be used, which may yield an information measure in bits.

The Shannon information metric may be additive. That is, metric information relating to information contained in two independent events can be summed. For example, for two independent events x and y:

$$p(x \text{ and } y) = p(x)p(y)$$

and so $$I(x \text{ and } y) = -\log p(x \text{ and } y) = -\log [p(x)p(y)] = -\log p(x) - \log p(y) = I(x) + I(y)$$

In certain embodiments, this additive property may allow for disclosure accounting to be performed relating to multiple queries, thereby providing a measure of an amount of unique information disclosed relating to a particular individual over time. Although certain embodiments of the disclosed systems and methods are discussed herein in connection with a Shannon information metric, it will be appreciated that in other embodiments the disclosed systems and methods may alternatively (or also) be used in connection with any other suitable information metric.

In one example, an allele may be equally likely to be an A or a G—that is, the probabilities of each of these events is 0.5. If an event "x" corresponds with "the allele is A" in a Beacon API response, then the information content of this event may be expressed as:

$$I(x) = -\log p(x) = -\log(0.5) = 1 \text{ bit.}$$

The possession of the A allele may be fairly common, occurring in half of all people, so it may not convey very much information relating to a particular individual. On the other hand, if an allele has a 95% chance of being G and a 5% chance of being T, more information is conveyed in an event "y" corresponding with "the allele is T" in a Beacon API response, which may be expressed as:

$$I(y) = -\log p(y) = -\log(0.05) = \sim 4.322 \text{ bits.}$$

A deterministic allele behaves as expected. Accordingly, an event "z" corresponding with "the allele is C" in a Beacon API response which occurs with probability 1.0 may be expressed as:

$$I(z) = -\log p(z) = -\log(1) = 0 \text{ bits.}$$

The information contained in the events may be additive, so an amount of information conveyed by the co-occurrence of the events x, y and z may be expressed as:

$$I(x \text{ and } y) = I(x) + I(y) = \sim 5.322 \text{ bits.}$$

Consistent with embodiments disclosed herein, this determined amount may be analyzed in relation to a disclosure budget and/or threshold, and access to a particular result and/or feature may be allowed, disallowed, and/or otherwise restricted based on the same.

Disclosure Budgets and Thresholds

An information metric consistent with embodiments disclosed herein may provide a metric used in connection with accounting for how much information about a particular individual has been revealed over time to one or more requesting users and/or limit and/or otherwise manage future disclosures. Consistent with embodiments disclosed herein, this metric may be compared against an allowed disclosure budget and/or threshold in connection with managing access decisions. It will be appreciated that the threshold and/or budget can be set to any suitable value, depending, for example, on a particular information metric used and/or the degree of reidentification risk that the system architect, system users, and/or other interested parties are willing to tolerate.

In some embodiments, the difficulty of ascertaining the informational value of an allele in connection with identifying a particular given individual (e.g., in a reidentification attack) may be associated with the "entropy" in the allele. For example, if an unknown allele is modeled as a random variable with a probability mass function defined by the allele frequencies in a given population, then the entropy of this random variable provides a measure of how much information there is inherent to this allele in connection with identifying a particular user—in other words, an upper limit, budget, and/or threshold on the possible disclosure. Information disclosed below the entropy limit may incrementally improve the ability of an adversary to guess the private value and/or succeed in a reidentification attack.

In certain embodiments, a disclosure budget and/or threshold may in essence specify a minimum on how much an adversary should be required to guess in order to learn private information relating to a dataset (e.g., identifying a particular individual's data as being included in a dataset). Disclosure budgets and/or thresholds may be set in a variety of ways. For example, a disclosure budget and/or threshold may be set by:

Setting a threshold that is some fraction of the highest theoretical disclosure relating to a particular individual.

Setting a threshold adaptively based on a rate of disclosure over time.

Setting disclosure thresholds that are tuned to the information disclosed in certain sensitive areas of a genome.

Establishing a global threshold for an entire dataset to mitigate mining of excessive information from a single dataset.

Establishing individual thresholds for individual potential queriers, possibly modeling collusion.

Queries to Individual Datasets

In some embodiments, a dataset may include information pertaining to only one individual. In certain embodiments using a Beacon API, limiting the disclosure of information about the individual may begin with an accounted disclosure of 0. At each query, the probability may be computed, based on an allele frequency in a given population, of two events: "yes, the individual has the allele" and "no, the individual does not have the allele." If the individual in question has the allele being queried, the accounted disclosure may be added to based on the information included in the corresponding event. If the disclosure would exceed a threshold and/or exhaust a budget of information release, the query may be ignored and/or responded to with a non-informative answer (i.e., "The query may not be answered" or the like.)

In one example, suppose an initial query relates to an allele that occurs with probability 0.2. If an individual has the allele, $-\log 0.2 = \sim 2.322$ bits may be added to the total accounted disclosure. If the individual does not have the given allele at the given position, $-\log (1-0.2) = -\log 0.8 = \sim 0.322$ bits may be added to the accounted disclosure. Failure to possess the allele—that is, an answer of "no"—may also convey information, because it may eliminate uncertainty about the individual in question. Accordingly, in some embodiments, disclosure accounting processes may account for the informational value that is both negative and positive.

In some circumstances, an attacker may inadvertently learn information when a disclosure threshold is crossed. For example, an attacker may conclude that their unsuccessful query contained more or less information than prior queries. If the attacker knows the disclosure accounting algorithm being employed and the allele frequencies being used, they may be able to determine the status of an individual. If the disclosure accounting process terminates responses regarding an individual once the threshold is exceeded and/or the budget is exhausted, this edge case may only occur once. In certain embodiments, lowering the disclosure threshold and/or budget may mitigate this circumstance.

Queries to Multiple Genomic Datasets

Certain datasets may include information pertaining to multiple individuals (e.g., a total of N individuals). In embodiments using a Beacon API, an initial accounted disclosure of 0 may be set for each individual included in the dataset. At each query, the probability that a given individual has the allele—call it p—and the probability that a given individual does not have the allele—that is 1−p—may be determined. For example, in one embodiment, if there are K individuals that have the allele being queried, for each of the K individuals, −(1/K) log p may be added to their total accounted disclosure. For individuals who do not possess the allele, −(1/(N−K)) log (1−p) may be added to their total accounted disclosure.

In some embodiments, this disclosure accounting methodology may "spread" the information disclosure over the number of actual matches. For example, if only one individual matches the query, that individual will bear all of the information loss. If two people match, the loss may be shared equally between them, and so forth.

In certain embodiments, this approach may be responsive to the idea that the most effective reidentification attacks may attempt to select the most unique (e.g., low-frequency) alleles for a given individual—that is, the ones that would likely not match any other members of the dataset. Such queries may thus count heavily against the targeted individual's total accounted disclosure. It will be appreciated, however, that other mechanisms for spreading the information loss across matches may alternatively (or in addition) be used in connection with the disclosed embodiments.

If an individual's disclosure threshold and/or budget is exceeded and/or exhausted, which may be different for different individuals, several policy-enforced actions may be taken including, for example:

Terminating or delaying responses to future queries.

Removing the given individual from the dataset, effectively shrinking the dataset to N−1 individuals.

Querier Information and Disclosure Accounting

In certain embodiments, information relating to a querier may be used in connection with disclosure accounting and policy enforcement processes consistent with embodiments disclosed herein. For example, a querier's stated identity, authenticated identity, and/or other proxies (e.g., a querier's IP address and/or user agent) may be used in connection with disclosure accounting methods. In one example, the above-described dataset including information pertaining to multiple individuals and methodology for accounting for disclosure in relation to the same may be used, but disclosure may be accounted and/or otherwise recorded in relation to a particular querier (e.g., as opposed to a global disclosure for all queriers). If a disclosure threshold relating to a particular individual is exceeded, the given individual can be removed from future queries by the particular querier, removed from all further queries, and/or the like. In this manner, disclosure budgets and/or thresholds may be associated with particular queriers alternatively or in addition to individuals associated with information included in the dataset.

Mitigating Collusion Attacks

In connection with a reidentification effort, attackers may choose to collude, separately issuing requests against datasets and receiving responses that may be combined to identify a particular individual within the dataset. In certain embodiments using a Beacon API, mitigating the potential for collusion attacks may begin with setting an initial accounted disclosure of 0 for each individual included in the dataset. A data structure (e.g., a matrix, graph, etc.) may be created that models the probability that a given querier will share data with each other querier. In some embodiments, the collusion may be modeled for each pair of queriers, with a fixed collusion probability, incorporating groups of researchers, and/or the like. It will be appreciated that a variety of collusion models may be used in connection with the disclosed embodiments.

In one example, the collusion probability between querier i and querier j may be denoted $c(i,j)$. For a query from querier i, an associated incremental disclosure may be determined (e.g., determined using the above-described methods). The incremental disclosure may be denoted as d. For each other potential colluder j, the incremental disclosure may be expressed according to $d*c(i, j)$ and recorded appropriately. This example assumes that the information shared with colluders is proportional to the probability of sharing, and accounts for such disclosure according to the same.

The above example models pairwise collusion between colluders i and j as a single matrix entry $c(i,j)$. However, under some collusion assumptions, there is little reason why j could not turn around and share information he has received from i with an additional colluder k. This is in addition to any information that i may share directly with k. This process can be iterated to allow information to propagate to all possible queriers. To model this scenario, a discrete Markov chain may be used, and in the limit, the steady-state sharing probabilities between two principals i and j may be determined by an eigenanalysis of the one-step collusion matrix.

Estimating Allele Frequencies

A variety of methods may be used for determining and/or otherwise estimating allele frequencies. The information inherent in an event may depend on the probability of the event. For example, the probability of the event "the given individual has base A in position 12,345,678 on chromosome 9" can be estimated by considering the relative frequency of this allele in the dataset, in the ethnic group of the individual, in the broader population, and/or the like.

Allele frequencies may be markedly different in different populations. An adversary may make more or less accurate predictions about an individual based on these allele frequencies. One approach to account for disclosed information consistent with embodiments disclosed herein includes determining the relative frequency of the allele in different datasets and taking the minimum (e.g., the most informative) allele frequency as a standard for determining the informational value of a particular disclosure. In some embodiments, the information disclosure computation may reflect probabilities known to an adversary. For example, if an adversary knows that a given individual is of Han Chinese ancestry—perhaps through some other metadata provided about the dataset—the allele frequencies used in the computation may reflect this knowledge.

Sensitive Variants

Different variants may be more sensitive than others. For example, with a Beacon API query, variants that are associated with Alzheimer's disease, schizophrenia, ethnicity, or eye color may be more sensitive than variants that are not associated with a clearly observable phenotype. Queries to variants with a strong phenotypical association could be used in connection with identifying targeted reidentification attacks against specific individuals. A variety of mechanisms for factoring in different sensitivities among variants may be used in connection with embodiments of the disclosed disclosure accounting processes, including, for example:

- Eliminating the sensitive variants entirely from the dataset and/or responding "No" for queries to such variants.
- Weighting sensitive variants more heavily by multiplying an associated information disclosure metric by a variable factor proportional to the sensitivity of the variant in question, thus increasing the metric of effective disclosure for sensitive variants.
- Modeling the probability that a particular observed phenotype can be used to infer a given variant and/or using this in determining a conditional information disclosure.

Modeling Knowledge of Attackers

In lieu of and/or in addition to determining information disclosure metrics solely based on allele frequencies, the knowledge of an adversary may be modeled in connection with embodiments of the disclosed disclosure accounting process. In some embodiments, the knowledge of the adversary may be accounted for based on the total information disclosed to a given querier and not necessarily based on any detailed information that might be uniquely held by the querier.

In some embodiments, the informational value of a disclosure of information may depend on the prior knowledge of the adversary. For example, if an adversary already knows the answer to a query, then the result of the query may not be additionally informative. If the adversary has knowledge that allows them to predict a response to a query, then the disclosure may be less informative than it might otherwise be.

In certain embodiments, incorporating additional information relating to a potential adversary may be accomplished using conditional information, which may be informally described as the informational value of one event given another event. For example, conditional information can be expressed as:

$$I(x|y) = -\log p(x|y).$$

In circumstances where the additional information known to an adversary may be modeled, the disclosure information metric determinations may use available conditional information. In some embodiments, conditional information may include, for example, information disclosed to given queriers over time, information from genomic studies indicating relations that may be inferred across variants, and/or the like.

Related Variants

In some circumstances, knowledge of one variant may convey information relating to another. Many variants may not be independent of one another. For example, because genetic recombination is an imperfect shuffling, the closer together two variants are on a chromosome, the more likely they may be inherited together. This phenomenon is known as linkage disequilibrium and may allow for predictions to be made about variants which are not specifically queried. For example, an individual's likelihood of having certain mutations associated with Alzheimer's disease may be predicted even when specific variants associated with Alzheimer's disease are not provided to queriers.

As a result of linkage disequilibrium, information disclosed relating to a particular variant may "leak" into other variants. For example, if an adversary knows that a database contains a variant v1 that is commonly associated with variant v2, then they may be receiving information about the one when they query the other. In other words, the events are not independent. Conditional information may be used in connection with modeling the joint probabilities of multiple variants (e.g., a pair of variants or the like), and information leakage for all variants that are in linkage disequilibrium with the variant actually queried can be determined and accounted for in connection with embodiments of the disclosed disclosure accounting processes.

Disclosure of Information Associated with Related Individuals

Genomic data is inherited from parents, and is shared with other relatives, so information revealed about a particular individual may also increase knowledge relating to that individual's relatives. Embodiments of the disclosure accounting systems and methods disclosed herein may thus further account for inheritance. A variety of approaches may be used to model inheritance in connection with the disclosed embodiments including, for example, relatively simple estimates based on distance of relationship to more complicated estimates that model the complex nature of genetic recombination, dominant and recessive traits, and/or the like. Embodiments of the disclosed systems and methods may account for leakage of information across relatives in a variety of ways, including, for example:

- For known relatives that share the same variants—especially when the adversary may know the relationship—incremental information disclosure may be added to the relative's total disclosure as well.
- The degree of relatedness among individuals may be modeled, and information disclosure may be added proportionally. This may involve modeling the ability of the adversary to infer variants of a relative given the relationship with the queried individual.

As in previous examples, individuals and/or their relatives can be removed from consideration in connection with queries to a dataset when disclosure thresholds are exceeded and/or disclosure budgets are exhausted.

Rate of Information Disclosure

A rate of information disclosure may be used in connection with disclosure accounting consistent with the disclosed embodiments. For example, queries returning information relating to a particular individual at a query rate over time that exceeds a threshold rate may result in access to that individual's data being restricted in some manner. Similarly, an amount of information disclosure in a given time period relating to a particular individual may be determined, and access to that individual's data may be restricted if the amount of disclosed information in the time period exceeds an associated budget and/or threshold.

Policy-Enforced Access Restrictions

As discussed above, in response to determining that a disclosure threshold has been exceeded and/or a disclosure budget associated with an individual in a dataset has been exhausted, access to the individual's data may be restricted and/or otherwise limited from consideration in connection with future queries to the dataset. Access to the individual's data may be restricted and/or limited to an individual querier, suspected colluders, and/or all queriers. In certain circumstances, however, removal of an individual's data from a dataset may allow an attacker to shrink the dataset and reduce its utility in connection with certain genomic investigations.

In some embodiments, rather than permanently restricting and/or limiting access to a user's data in a dataset, the individual's data may be reintroduced for use in connection with queriers according to defined criteria. Examples of such criteria include, for example, reintroducing an individual's data:

After some fixed period of time has elapsed.
After a variable period of time has elapsed, the period being a function of the amount or rate of disclosure.
After a period of time in which no further sensitive queries against the individual have been made.
Based on a model in which the disclosure "decays" over time, modeling the tendency of adversaries (especially non-malicious adversaries) to forget the information disclosed.
Based on a model of the difficulty of making inferences from the information actually disclosed.

Information Metrics and Entropy

Certain examples described above may use the Shannon metric to quantify disclosure. In a sense, information measures the degree of "surprise" that an event has occurred; a certain event (probability 1.0) has a surprise factor of 0, and an extremely rare event has a very high surprise value. A closely related metric is the notion of Shannon entropy, which serves as a way to measure the uncertainty in a random variable. Each value that can be taken on by a random variable represents an event, and that event carries an amount of information based on its probability of occurrence. The entropy of a random variable is the expected information in the random variable. For example, if a discrete random variable X takes on values x1, x2, . . . , xn, then the entropy of X may be expressed according to:

$$H(X)=-\text{Sum } i=1 \text{ to } n[p(X=xi)\log p(X=xi)]$$

Consistent with embodiments of the disclosed systems and methods, a particular allele may be considered to be a random variable. The distribution of bases may thus reflect the allele frequency in some population. Based on such a distribution, the entropy for the given allele may be determined. Models for determining allele frequency in a population may incorporate linkage disequilibrium models, allele frequencies in different populations, and/or the like. Regardless of the specific model employed, the entropy may represent the uncertainty as to the value of the random variable before any queries are performed. As queries are answered, the uncertainty about the random variable is gradually reduced. Disclosure accounting methods consistent with the disclosed embodiments may thus be based on the remaining uncertainty in the random variable.

Mutual Information

The concept of mutual information may be used in connection with determining entropy of a variable. For example, the mutual information in two random variables may be used to model the way in which knowledge of one of the random variables reduces uncertainty in another. As an example, if A represents a random variable for an allele, and C is a random variable that captures the result of a query or computation, then the mutual information between these two random variables may be expressed as:

$$I(A;C)=H(A)-H(A|C)$$

That is, the mutual information is the uncertainty in A reduced by the uncertainty in A given the value of C. Mutual information may provide a general way to model the reduction in uncertainty as more and more queries about sensitive values are answered in connection with embodiments of the disclosed disclosure accounting processes.

In some embodiments, incorporating mutual information into the disclosed systems and methods may involve initializing with a stored variable containing an initial amount of uncertainty, which may depend upon the a priori distribution of the random variable. In responding to a query, the reduction in uncertainty may be determined and subtracted from the variable. When the remaining uncertainty reaches zero, the value of the random variable has been fully disclosed. Further disclosures may thus be harmless, as the adversary/querier would now know the value deterministically.

Information entropy may, for example, be used in connection with any of the various embodiments of disclosure accounting processes described above. For example, in some embodiments, an information budget (e.g., the remaining uncertainty in a sensitive value) may be kept for each pair of sensitive values, queriers, etc. in connection with mutual information modeling. Mutual information modeling may similarly be extended to model collusion, querier forgetfulness of prior results, and/or the like.

In one example, a service may wish to provide an indication of a probability that the offspring of two individuals will be born with a specific genetic disorder, such as Tay-Sachs disease, but may not wish to reveal individual carrier status. In this example, if both parents are carriers, their offspring have a 25% chance of having the disease and a 50% chance of being a carrier. If neither of the individuals are carriers, their offspring have no chance of having the disease or being a carrier.

In certain populations, the probability of being a carrier of variants relating to Tay-Sachs disease may be one in 27. Accordingly, the probabilities of being a carrier and not being a carrier for any individual in the population may be expressed as:

$$P(\text{carrier})=1/27 \text{ and } P(\text{non-carrier})=26/27$$

The entropy for this distribution may be expressed according to:

$$H(A)=-1/27*\log(1/27)-26/27*\log(26/27)$$

$$H(A) \sim 0.2285 \text{ bits}$$

Information disclosure loss from a computational result may be reflective of a reduction in the uncertainty of unknown information used in the computation. This may be expressed as:

$$I(A;C)=H(A)-H(A|C)$$

where C is a random variable representing a result of the computation and A is the unknown information used in the computation to generate the result. If an individual possesses knowledge of C and the computation, the uncertainty of the unknown information A is thus reduced.

In the above example relating to the Tay-Sachs disease carrier status of two individuals in a population where the probability of being a carrier is 1/27, the information disclosure loss following a computation may be determined as follows:

$$P(A|C=\text{true})=1.0$$

$$H(A|C=\text{true})=0.0 \text{ bits}$$

$$I(A;C=\text{true}) \sim 2.2854 \times 10^{-1} \text{ bits}$$

$$P(A|C=\text{false}) \sim 3.7 \times 10^{-2}$$

$$H(A|C=\text{false}) \sim 2.2228 \times 10^{-1} \text{ bits}$$

$$I(A;C=\text{false}) \sim 6.25 \times 10^{-3} \text{ bits}$$

$$I(A;C) \sim 6.55 \times 10^{-3} \text{ bits}$$

In this example, information loss between the two individuals may be symmetric as both individuals are from the same population with the same probability of being a carrier. In another example, the likelihood of one individual being a carrier may be $\frac{1}{27}$ and the likelihood of another individual being a carrier may be $\frac{1}{2000}$. The information loss between these two individuals would thus be asymmetric given the varied input distribution, as shown below:

$$I(A;C=\text{false}) \sim 8.383 \times 10^{-5} \text{ bits}$$

$$I(B;C=\text{false}) \sim 2.035 \times 10^{-4} \text{ bits}$$

Figure 3:
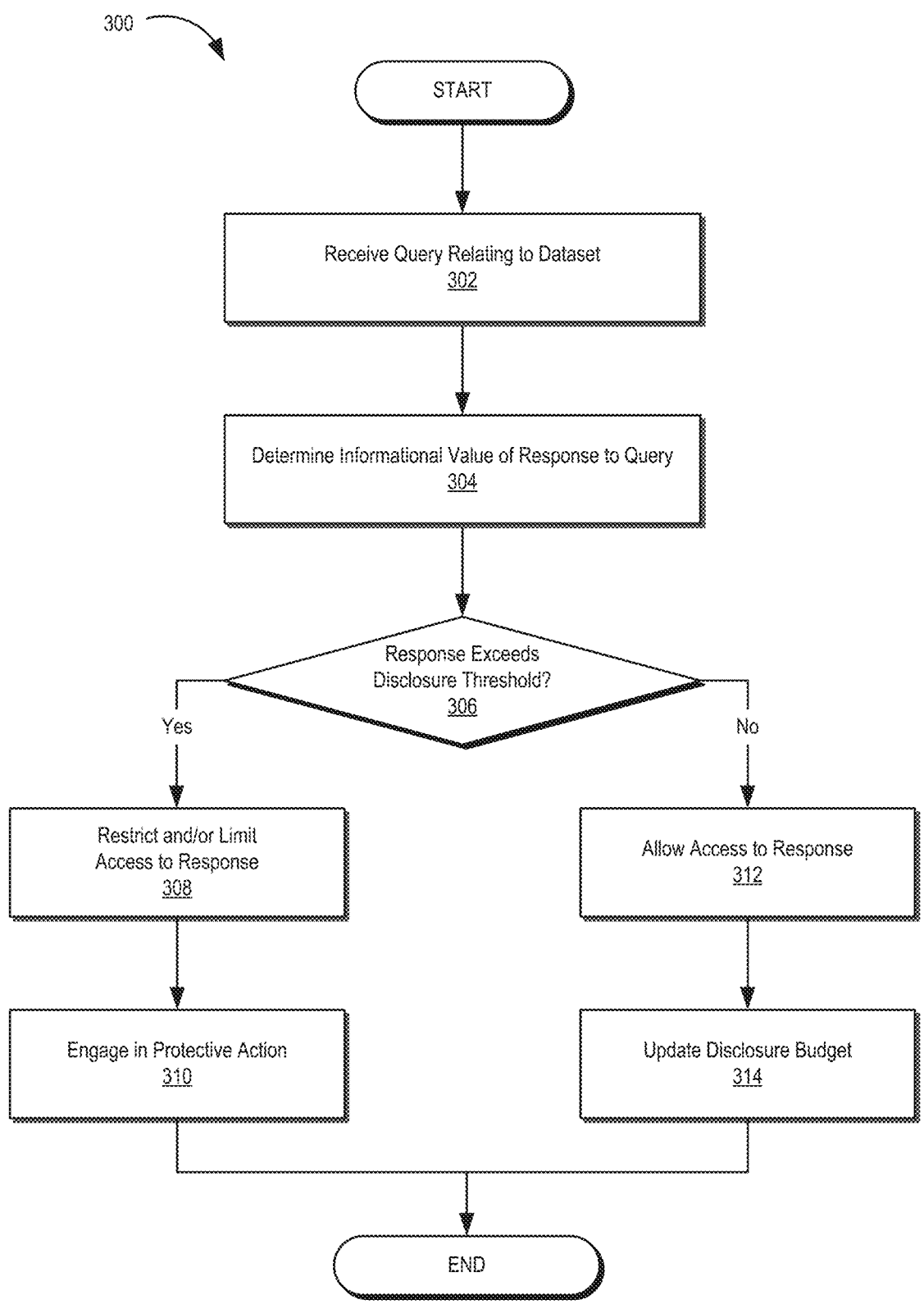
FIG. 3 illustrates a flow chart of an exemplary disclosure accounting method consistent with embodiments disclosed herein.

FIG. 3 illustrates a flow chart of an exemplary disclosure accounting method 300 consistent with embodiments disclosed herein. The illustrated method 300 may be implemented in a variety of ways, including using software, firmware, hardware, and/or any combination thereof. In certain embodiments, the method 300 and/or its constituent steps may be performed by a resource service, one or more remote systems, and/or any other suitable system or combination of systems.

In certain embodiments, the illustrated method 300 may facilitate among other things, receiving and generating responses to requests for computations based on a dataset that may include genomic information, determining an informational value of the responses (e.g., based on a calculated informational metric and/or entropy), comparing this value to a threshold and/or budget to determine whether the response should be provided to a requesting querier, and enforcing rules and/or policies associated with the dataset and/or the disclosure accounting processes.

At 302, a query may be received requesting a result of a computation based on a dataset that may, in certain embodiments, include genomic information relating to one or more individuals. The query may be received by a resource service and/or by a secure computing environment configured to securely process genomic data. In some embodiments, the query may comprise a Beacon API query. For example, the query may ask whether the dataset includes any genomes with a particular allele in a particular position. The query may pertain to the entire dataset and/or a subset thereof.

The query and/or an associated computational result or response may be analyzed at 304 to determine an amount of disclosure and/or an informational value associated with the result. The informational value associated with a result may be determined using any of the methods described herein and/or various combinations of the same. For example, in certain embodiments an information metric, such as a Shannon information metric, may be used to reflect an amount of disclosure and/or the informational value associated with a particular result. In further embodiments, a measure of informational entropy may be used to model the informational value associated with a result by modeling a level of remaining uncertainty of information included in the dataset used to generate the result. It will be appreciated that any suitable method and/or model for determining an amount of disclosure and/or the informational value associated with a result and/or combinations thereof may be used in connection with embodiments of the disclosed systems and methods At 306, the determined amount of disclosure and/or informational value may be analyzed in connection with a disclosure budget and/or threshold to determine whether access to the result should be allowed, disallowed, and/or otherwise restricted. For example, it may be determined that providing the result to the querier would exceed a disclosure threshold and/or exhaust a disclosure budget relating to the querier, one or more individuals associated with data used to generate the result, and/or the like. If so, the method 300 may proceed to 308, were access to the result may be restricted and/or otherwise limited in some way (e.g., by filtering the result, adding noise, etc.). In addition, in some embodiments, at 310, one or more additional protective actions may be taken to preserve the privacy of individuals associated with the applied disclosure budget and/or thresholds. For example, an individual's data may be removed from consideration in connection with future queries to the dataset, a particular querier may be denied future access to the dataset, and/or the like.

If it is determined that providing the result to the querier does not exceed the disclosure threshold and/or exhaust the disclosure budget relating to the querier, one or more individuals associated with the data used to generate the result, and/or the like, the method may proceed to 312, where the result may be provided to the querier. In addition, at 314, disclosure budget information associated with the querier, and/or the one or more individuals associated with the data used to generate the result, may be updated to reflect the relative informational value associated with the disclosed result.

Figure 4:
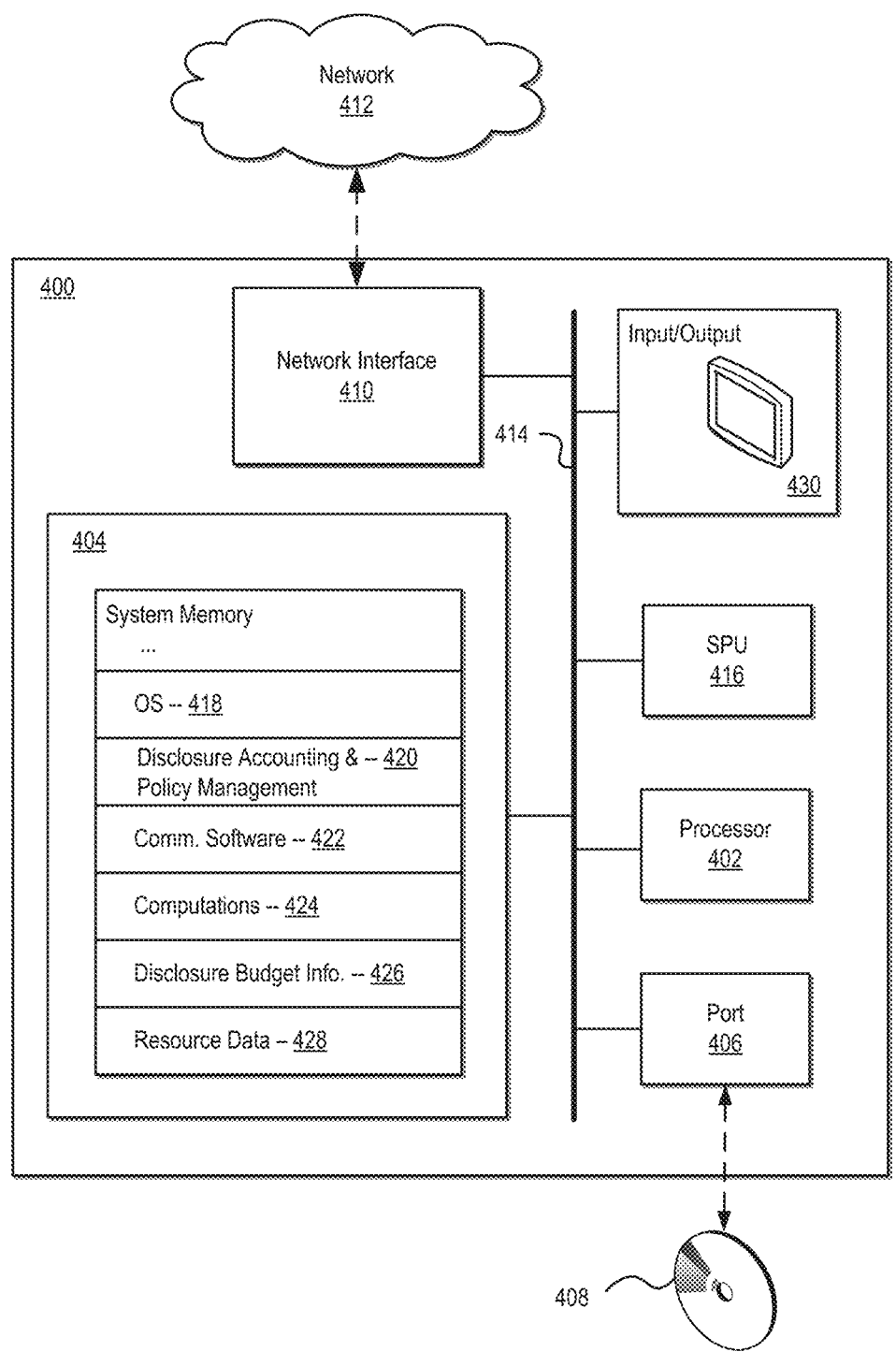
FIG. 4 illustrates an exemplary system that may be used to implement embodiments of the systems and methods of the present disclosure.

FIG. 4 illustrates an exemplary system 400 that may be used to implement embodiments of the systems and methods disclosed herein. The exemplary system 400 may comprise a device and/or a computer system that may perform various aspects of the operations disclosed herein. As illustrated in FIG. 4, the system 400 may include: a processing unit 402; system memory 404, which may include high speed random access memory ("RAM"), non-volatile memory ("ROM"), and/or one or more bulk non-volatile computer-readable storage mediums (e.g., a hard disk, flash memory, etc.) for storing programs and other data for use and execution by the processing unit 402; a port 406 for interfacing with removable memory 408 that may include one or more diskettes, optical storage mediums, and/or other computer-readable storage mediums (e.g., flash memory, thumb drives, USB dongles, compact discs, DVDs, etc.); a network interface 410 for communicating with other systems via one or more network connections 412 using one or more communication technologies; a user interface 430 that may include a display and/or one or more input/output devices such as, for example, a touchscreen, a keyboard, a mouse, a track pad, and the like; and one or more busses 414 for communicatively coupling the elements of the system 400.

In some embodiments, the system 400 may, alternatively or in addition, include a SPU 416 that is protected from tampering by a user of system 400 or other entities by utilizing secure physical and/or virtual security techniques. An SPU 416 can help enhance the security of sensitive operations such as trusted credential and/or key management, secure genomic data management and/or computations in connection with the same, and other aspects of the systems and methods disclosed herein. In certain embodiments, the SPU 416 may operate in a logically secure processing domain and be configured to protect and operate on secret information. In some embodiments, the SPU 416 may include internal memory storing executable instructions or programs configured to enable the SPU 416 to perform secure operations. For example, in some embodiments an SPU 416 such as described in commonly-assigned U.S. Pat. No. 7,430,585 entitled "Secure Processing Unit Systems and Methods," and filed Sep. 27, 2006 ("the '585 patent"), and/or U.S. Pat. No. 5,892,900 entitled "Systems and Methods for Secure Transaction Management and Electronic Rights Protection," and filed Feb. 13, 1995 ("the '900 patent") (the contents of the '585 patent and the '900 patent hereby being incorporated by reference in their entireties), could be used.

The operation of the system 400 may be generally controlled by a processing unit 402 and/or a SPU 416 operating by executing software instructions and programs stored in the system memory 404 (and/or other non-transitory computer-readable media, such as removable memory 408). The system memory 404 may store a variety of executable programs or modules for controlling the operation of the system 400. For example, the system memory 404 may include an operating system ("OS") 418 that may manage and coordinate, at least in part, system hardware resources and provide for common services for execution of various applications and a policy management and/or disclosure accounting module 420 configured to manage and/or enforce policies and/or rules associated with genomic and/or other bioinformatic data and/or implement embodiments of the disclosed disclosure accounting processes. The system memory 404 may further include, without limitation, communication software 422 configured to enable in part communication within and by the system 400, computations 424 (e.g., computations configured to operate on genomic data or the like), disclosure budget and/or threshold information 426 used in connection with disclosure accounting access management decisions, resource data 428 that may include genomic data, and/or any other suitable module and/or modules configured to implement various aspects of the disclosed embodiments.

The systems and methods disclosed herein are not inherently related to any particular computer, electronic control unit, or other apparatus and may be implemented by a suitable combination of hardware, software, and/or firmware. Software implementations may include one or more computer programs comprising executable code/instructions that, when executed by a processor, may cause the processor to perform a method defined at least in part by the executable instructions. The computer program can be written in any form of programming language, including compiled or interpreted languages, and can be deployed in any form, including as a standalone program or as a module, component, subroutine, or other unit suitable for use in a computing environment. Further, a computer program can be deployed to be executed on one computer or on multiple computers at one site or distributed across multiple sites and interconnected by a communication network. Software embodiments may be implemented as a computer program product that comprises a non-transitory storage medium configured to store computer programs and instructions, that when executed by a processor, are configured to cause the processor to perform a method according to the instructions. In certain embodiments, the non-transitory storage medium may take any form capable of storing processor-readable instructions on a non-transitory storage medium. A non-transitory storage medium may be embodied by a compact disk, digital-video disk, a magnetic tape, a magnetic disk, flash memory, integrated circuits, or any other non-transitory digital processing apparatus memory device.

Although the foregoing has been described in some detail for purposes of clarity, it will be apparent that certain changes and modifications may be made without departing from the principles thereof. It should be noted that there are many alternative ways of implementing both the systems and methods described herein. Accordingly, the present embodiments are to be considered as illustrative and not restrictive, and the invention is not to be limited to the details given herein, but may be modified within the scope and equivalents of the appended claims.

What is claimed is:

1. A method for protecting personal information, the method performed by a system comprising a processor and a non-transitory computer-readable medium storing instructions that, when executed by the processor, cause the system to perform the method, the method comprising:
   receiving a first request from a user system to perform a first computation by the system on a genomic dataset, the genomic dataset comprising genomic information associated with a plurality of individuals;
   generating a first response to the first request by performing the first computation on the genomic dataset;
   determining a first informational value of the first response relating to at least one individual associated with the genomic dataset;
   determining, based on the first informational value and a disclosure budget associated with the at least one individual, that permitting access to the first response to the user system does not exhaust the disclosure budget;
   wherein the disclosure budget is generated based on a statistical indication of a uniqueness of information associated with the at least one individual included in the dataset relative to information associated with other individuals of the plurality of individuals;
   permitting access to the first response by the user system based at least in part on determining that providing the first response to the user system does not exhaust the disclosure budget;
   updating the disclosure budget based on the first informational value;
   receiving a second request from the user system to perform a second computation by the system using the genomic dataset;
   generating a second response to the second request by performing the second computation using the genomic dataset;
   determining a second informational value of the second response relating to the at least one individual associated with the genomic dataset;
   determining, based on the second informational value and the disclosure budget associated with the at least one individual, that permitting access to the second response to the user system would exceed the disclosure budget;
   restricting access to the second response by the user system based at least in part on determining that providing the second response to the user system would exceed the disclosure budget; and
   engaging in at least one action to protect the privacy of the at least one individual, wherein restricting access to the second response comprises at least one of:
   returning an indication to the user system that the second request cannot be responded to, filtering the second response prior to transmission to the user system, and adding noise to the second response prior to transmission to the user system.

2. The method of claim 1, wherein the first informational value comprises an informational metric.

3. The method of claim 2, wherein the informational metric comprises a Shannon information metric.

4. The method of claim 1, wherein the first informational value is based on a statistical significance of the first response relative to the genomic dataset.

5. The method of claim 1, wherein the informational value comprises an indication of a reduction in informational entropy associated with the at least one individual in the genomic dataset based on the first response.

6. The method of claim 1, wherein the at least one action comprises removing information associated with the at least one individual from the genomic dataset.

7. The method of claim 6, wherein removing the information comprises removing the information associated with the at least one individual from the genomic dataset for a period of time.

* * * * *